United States Patent [19]
Anders

[11] Patent Number: 5,492,470
[45] Date of Patent: * Feb. 20, 1996

[54] DENTAL IMPLANT WITH SHOCK ABSORBENT CUSHIONED INTERFACE

[76] Inventor: Irving Anders, 54 Crossway, Scarsdale, N.Y. 10583

[*] Notice: The portion of the term of this patent subsequent to Jun. 20, 2012, has been disclaimed.

[21] Appl. No.: 303,537

[22] Filed: Sep. 9, 1994

Related U.S. Application Data

[62] Division of Ser. No. 237,220, May 3, 1994, Pat. No. 5,425,639.

[51] Int. Cl.⁶ .................................................. A61C 13/28
[52] U.S. Cl. .................................. 433/169; 433/173
[58] Field of Search .................................. 433/169, 173, 433/174, 175, 176, 201.1

[56] References Cited

U.S. PATENT DOCUMENTS

| | | | |
|---|---|---|---|
| 3,934,347 | 1/1976 | Lash et al. | 433/201.1 |
| 3,955,280 | 5/1976 | Sneer | 433/174 |
| 4,195,409 | 4/1980 | Child | 433/201.1 |
| 4,270,905 | 6/1981 | Mohammed | 433/201.1 |
| 4,531,916 | 7/1985 | Scantlebury | 433/173 |
| 4,552,532 | 11/1985 | Mozsary | 433/174 |
| 4,568,285 | 2/1986 | Chiaramonte et al. | 433/169 |
| 4,622,010 | 11/1986 | Koch | 433/173 |
| 4,780,080 | 10/1988 | Haris | 433/173 |
| 5,052,931 | 10/1991 | Kirsch | 433/174 |

FOREIGN PATENT DOCUMENTS

| | | | |
|---|---|---|---|
| 2017127 | 10/1992 | WIPO | 433/173 |
| 3017634 | 9/1993 | WIPO | 433/172 |

*Primary Examiner*—Cary E. O'Connor
*Attorney, Agent, or Firm*—Lackenbach Siegel Marzullo Aronson & Greenspan

[57] ABSTRACT

A dental implant device which effectively and physiologically prevents the penetration of bacteria and other microorganisms and foreign material into the vital implant interface surface with the bone while maintaining resilience and energy absorbing properties which prevent excessive stress on the implant and underlying bone tissue and discomfort to the user. This dental implant device comprises (a) a root structure made of a suitable dental prosthesis material, (b) a resilient boot member surrounding and in contact with the lower portion of the root structure, (c) a biocompatible substantially non-porous sheath member to which bony tissue will readily adhere, enclosing both the resilient boot member and lower portion of the root structure, and (d) a porous sleeve that prevents the penetration of pathogens into the vital implant interface with the bone. More preferably, the device includes a resilient membrane sleeve around an upper portion of the root structure and a seal between the upper and lower portions of the root structure and the sheath member to preclude tissue adherence to the boot member and prevent gingival tissue adherence to the sheath member.

21 Claims, 1 Drawing Sheet

DENTAL IMPLANT WITH SHOCK ABSORBENT CUSHIONED INTERFACE

This is a division of application Ser. No. 08/237,220 filed May 3, 1994, now U.S. Pat. No. 5,425,639.

FIELD OF THE INVENTION

The present invention relates to a dental implant and in particular to a dental implant with a shock absorbent cushioned interface between the implant and the embedding alveolar process, and a more physiological gingival attachment.

DESCRIPTION OF THE RELATED ART

Normally a living tooth has a root which rests in the periodontal membrane between the root of the tooth and the jaw. This membrane consists of millions of tiny fibers that together provide a cushion which spreads and distributes the impact force transmitted from the tooth to the jaw during mastication. In other words it acts as a shock absorber and has a damping effect on the impact force which the tooth receives thus providing a degree of flexibility between the tooth and the alveolar process of the jaw. The gingival tissue connects to the top of the root, sealing it from the oral fluids and pathogens.

Conventional dental implants rely on direct adhesion of bone tissue to the implant without the intervening periodontal membrane. Without the cushioning effect of the periodontal membrane the impact stress concentrations which the jaw bone encounters from an implant often result over time in bone resorption and loosening of the implant or trauma to the overlying soft tissue.

The dental community over the past forty years has attempted to develop endosseous and subperiosteal dental implants which could be considered successful and effective. The 1978 NIH-Harvard Consensus Development Conference recommended that only those implants which provide functional service for five years in 75 percent of the cases be considered successful (Schnitman, P. A. and Schulman, L. B. eds; Dental Implants Benefit and Risks; Department of Health and Human Resources, 1980, p. 329). The American Dental Association indicates that as many as 60 percent of the currently used endosseous and unilateral subperiosteal implants have failed after only two years or less (American Dental Association, Dentist's Desk Reference: Materials, Instruments and Equipment, 1981, p. 149).

Endosseous implants lie in the jaw bone. The portion of these implants which is positioned beneath the gum tissue (gingival tissue) in the jaw bone is the root portion. The upper portion of the endosseous implant extends through the gum tissue into the mouth to support artificial teeth and other dental devices. Endosseous implants are made of metallic, ceramic, or polymeric materials.

Dental implants are typically made of mechanically suitable and biocompatible materials. Biocompatible materials do not corrode in the oral environment or adversely affect either the soft or bony tissue of the mouth. Mechanically suitable materials withstand the normal forces of chewing without bending, fracturing, or otherwise becoming mechanically compromised. Suitable materials which have been previously developed include: metals, such as cobalt chromium alloys, stainless steels, and titanium or titanium alloys; ceramic, such as aluminum oxide or hydroxylapatite; and several polymers and carbon compositions.

As time progressed, implantation techniques and endosseous implant designs have been refined. Early trials revealed that implants had to be inserted firmly in sufficient volumes of mandibular or maxillary bone. Implants placed loosely in a bone socket became surrounded by fibrous tissue and through progressive movement failed. Thick or large diameter implants placed in thin, bony ridges were not supported by sufficient volumes of bone. Implants with sharp edges or undercuts in the root portion produced stress concentrations which destroyed surrounding bone (bone resorption). Accordingly, endosseous dental implants must be in tight fitting bony sockets and have small diameter or thin wedge-shaped designs for suitable stress distribution. Given these design and implant considerations, bone is most likely to closely appose and support (ankylose) the root structure of an implant.

More recently, problems at the gingival tissue/implant interface have been addressed. In the human, natural teeth and gingival tissue form a seal where the teeth pass through the gingival tissue. This area of sealing is known as the pergingival site. At the pergingival site, gingival connective tissue, and in particular gingival epithelium (the protective layer of cells on the surface of the gingiva), join with the surface layer of the tooth, thus isolating the underlying soft and bony tissues from the oral environment. Early prosthetic dental implants did not seal where they passed through the gingival tissue and consequently left underlying tissues susceptible to foreign materials, including bacteria.

U.S. Pat. No. 4,531,916, issued to T. V. Scantlebury et at, discloses a dental implant providing an improved seal at the pergingival site, i.e. the area where the teeth pass through the gingival tissue. This dental implant device includes a root structure, a cervical segment which is connected to and projects above the root structure, and a gingival interface. The non-physiological gingival interface is formed of expanded polytetrafluoroethylene having a porous microstructure for the ingrowth of connective tissue. The root structure may be porous or non-porous. Where porous, there is an ingrowth of bony tissue into the root structure, where non-porous, the bone should grow so that the root structure becomes ankylosed in the jaw bone. Ingrowth of bony tissue into the root structure or ankylosis results in a structure which has poor energy absorption properties and the interface becomes increasingly rigid over time. Mechanical forces generated during mastication result in increased stress and wear on the dental implant and increased discomfort to the user.

The dental implant according to present invention provides an improved more physiological gingival interface which prevents bacterial penetration while retaining resiliency where the implant extends into the oral cavity. In addition, the invention provides the missing cushion effect naturally provided by the periodontal membrane.

SUMMARY OF THE INVENTION

The present invention thus provides a dental implant which effectively prevents the penetration of bacteria and other microorganisms and foreign matter into the implant while maintaining resilience and energy absorbing properties which prevent excessive wear and stress and discomfort to the user.

These and other objects of the invention are achieved in a dental implant which includes a root structure made of a suitable dental prosthetic material and a resilient, compliant boot member which surrounds and is in contact with a lower portion of the root structure. Both the root structure and the resilient boot member are substantially enclosed by a preferably non-porous, cushioning sheath member which is compatible with and to which bony tissue has an attachment affinity. To seal the root structure from the oral environment, a sleeve of porous membrane material is secured to the upper portion of the root structure. The gingival tissue grows into and attaches to this sleeve and the upper portion of the root structure. A seal is also provided between the porous membrane and the boot member to prevent bony or gingival tissue from adhering to the boot member. Further objects, features and advantages of the invention will become more apparent from a reading of the following Detailed Description when taken in conjunction with the accompanying Drawing.

DETAILED DESCRIPTION OF THE PREFERRED EMBODIMENTS

Figure 1:
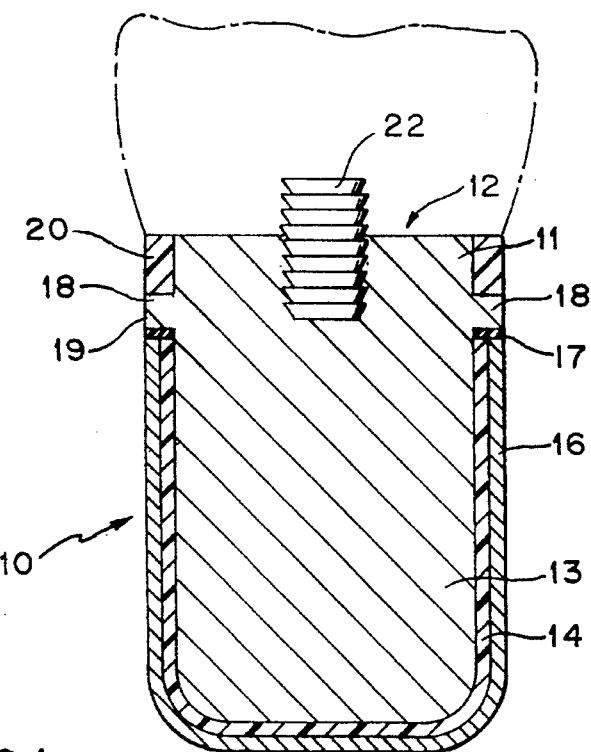
FIG. 1 is a cross-sectional view of a first preferred embodiment of the invention.

A dental implant device 10 in accordance with a first embodiment of the invention is shown in FIG. 1. The device 10 includes an elongated generally cylindrical root structure 12 which has an upper portion 11 adapted to receive a tooth crown or other prosthesis (shown in phantom). The root structure 12 may alternatively have a conical or any other conventional root shape as required by the particular tooth location or prosthesis design. The cylindrical shape is for illustrative purposes only.

Surrounding and in direct contact with a lower portion 13 of the root structure 12 is resilient and compliant boot member 14. The resilient boot member 14 is in turn enclosed in a close fitting biocompatible, substantially non-porous, cushioning sheath member 16. Between the upper portion 11 and the lower portion 13 of the root structure 12 is an annular collar 18. Collar 18 is preferably an integral part of the root structure 12 and has a smooth outer surface 19 and is of sufficient height to substantially prevent attachment of gingival or bone tissue thereto. The collar 18 may alternatively be a separate member which is adhesively or mechanically bonded to the root structure 12. The outer surface of collar 18 must be polished or otherwise rendered smooth to inhibit adhesion to the collar 18 by the gingival or bone tissue.

A ring or sleeve shaped, porous, resilient member 20 is attached around the outer surface of the upper portion 11 of the root structure 12 adjacent to the collar 18. This resilient member 20 is preferably adhesively or otherwise bonded to the surface of the upper portion 11.

The root structure 12 of the invention can be made of any suitable dental prosthetic material including metals, ceramics or synthetic polymeric materials. Metals include, but are not limited to, titanium and titanium alloys, chromium alloys, tantalum and stainless steels. Aluminum oxide is a suitable ceramic. Suitable polymeric materials include polyacrylates and polymethacrylates among others. The materials may be used singularly or in any combination thereof. The root structure 12 may be solid as shown, or it may be hollow or internally porous depending upon the particular material and service required.

The resilient and compliant boot member 14 may preferably be made of a synthetic, open-celled or closed-celled semi-permeable material having cushiony and/or foamy character or texture. Alternatively it may be made of an elastomeric material such as silicone rubber. The boot member 14 serves as a shock absorber which spreads impact force from the implant to the surrounding alveolar process over a brief time span. Thus, the patient senses a more physiologic, realistic natural sensation of force convergence more closely simulating that of a natural tooth, in contrast to the instantaneous fixed loading condition experienced with dental implant devices currently available. Suitable materials include flexible foams made of polytetrafluoroethylene (PTFE), polyurethanes and natural and synthetic rubbers, and polymeric materials. Generally any biocompatible material which exhibits a cushioning affect under stress will work. A preferred embodiment is expanded polytetrafluoroethylene (PTFE) which is an inert and biocompatible material with a history of medical implant use. U.S. Pat. Nos. 3,953,566 and 4,187,390 teach methods for producing expanded PTFE and characterize its porous structure. The thickness of the resilient boot member 14 may be from 0.1 to 2 mm thick, preferably at least about 0.5 mm thick.

The resilient boot member 14 is preferably securely attached to the root structure, for example by mechanical or adhesive means. The adhesive should be a type which will form a secure bond and should be a biologically acceptable medical adhesive. Silicone based adhesives obtained from Dow Corning are of a generally acceptable type for this application. Due to the properties of PTFE, bonding is difficult unless bonding sites are provided on the surface of the lower portion 13 off the root structure 12. A suitable etchant to form these sites is available is Tetraetch™ from W. L. Gore & Associates, Inc.

The lower portion 13 of root structure 12 and the boot member 14 are enclosed in a non-porous, cushioning sheath member 16 to preclude the lower portion 13 of the root structure 12 from contact with the surrounding bone tissue. The bone tissue in turn adheres solidly to the roughened outer surface of the sheath member 16. The non-porous sheath member 16 is made of a biocompatible material to which bony tissue has an affinity and will readily attach. To expedite this affinity, the outer surface of sheath member 16 interfacing with the bony tissue is roughened by conventional methods. Suitable materials include those which are presently used to form the root structures of dental implant devices such as titanium and titanium alloys, chromium alloys, tantalum and stainless steels; ceramics including aluminum oxide; and polymeric materials polyurethanes, polysulfones, polycarboxylates, perfluorinated polymers, such as polytetrafluoroethylene and fluorinated ethylene propylene, polyacrylics, silicone, etc. A preferred embodiment as a material of construction is titanium and its alloys. This sheath member may be from 0.1 to 2 mm thick, preferably at least 0.5 mm thick.

The non-porous, cushioning sheath member 16 and the resilient porous boot member 14 are in direct contact with each other to provide effective energy absorption properties, and are preferably connected together, for example, mechanically or adhesively. The adhesives referred to previously may be used here.

A seal means for sealing the boot member 14 which is mostly enclosed by the sheath member 16 from the porous ring 20 which surrounds the upper portion 11 of root structure 12 is provided by the collar 18. An interfacing seal between the porous collar 20 and the boot member 14 is accomplished by either mechanical means, chemical means or thermal means so as to prevent any ingrowing gingival tissue in the porous ring 20 from reaching and growing into the boot member 14. In this first embodiment, this seal is provided by the collar 18 and a heat sealed upper end 17 of the boot member 14 as explained below.

The collar 18 of the root structure 12 is non-porous, has a smooth outer surface 19, and is made of a biocompatible material such as those used for the non-porous sheath member 16. The smooth surface 19 functions as a deterrent to the upward growth of bony tissue and prevents the downward growth or adhesion of gingival tissue onto the collar 18. The collar 18 is preferably an integral part of the root structure 12 or it may be formed separately and attached or affixed to the root structure 12. The collar 18 protrudes from the root structure 12 a sufficient distance to cover the upper end of the sheath 16.

The upper end of the sheath 16 is spaced from the collar 18 by a flange shaped upper end 17 of the boot member 14 which radially extends outward over the upper end of the sheath 16 to provide a cushion between the root structure 12 and the sheath 16 in the vertical direction. The outer surface of the upper end 17 is preferably seared so as to seal and close off the top ends of the boot member and the sheath if a porous material, such as expanded PTFE, is used. Alternatively the upper end 17 may be a separate washer of biocompatible resilient material to which tissue will not adhere or penetrate such as silicone rubber. It is necessary to treat the porous surfaces where potential undesirable penetration through the porous surface might occur. This prevents or negates the entry of living cells, e.g. gingival tissue, bone tissue, and pathogens through the treated surface. Such porous surfaces may be treated by heating (searing the surface), chemically sealing, or with a adhesive to render the surface impenetrable to living cells and pathogens.

A resilient porous membrane 20 is attached to the upper portion 11 of root structure 12 adjacent to the collar 18. The resilient membrane 20, when ingrown with gingival tissue and attached to the gingival tissue, provides an effective seal between the underlying bone tissue and the oral environment of the mouth. This barrier prevents foreign materials including bacteria from passing into the underlying soft and bony tissues. As biocompatibility and sterility are of prime importance, a preferred material is expanded polytetrafluoroethylene. Various expanded PTFE in suitable densities and pore sizes are available commercially as "Goretex" from the W. L. Gore & Associates, Inc. of Newark, Del., the United States of America.

The dental implant device 10 includes a serrated, ribbed or threaded post 22 projecting from the upper portion 11 for attachment of a dental prosthesis or artificial tooth, shown as a phantom line in the Figures.

Figure 2:
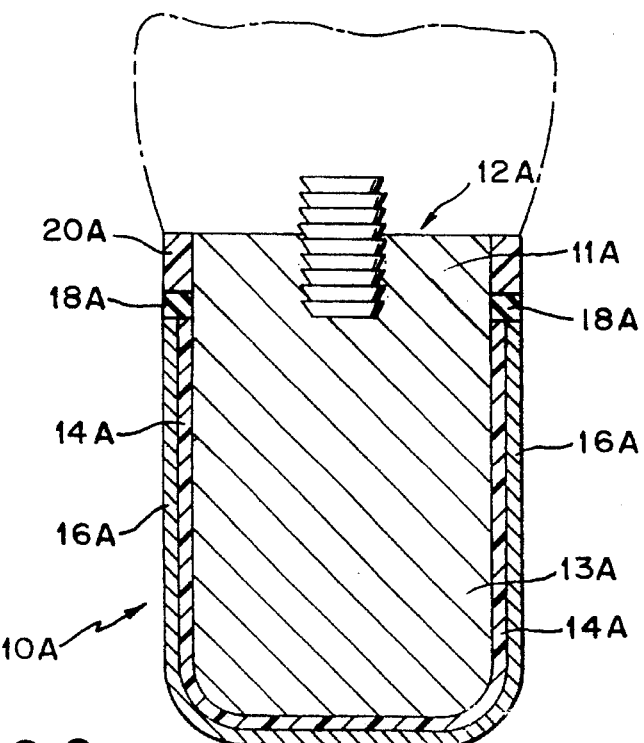
FIG. 2 is a cross-sectional view of a second preferred embodiment of the invention.

An alternative preferred embodiment of the implant device 10A is shown in FIG. 2. The device 10A includes a root structure 12A which has an upper portion 11A and a lower portion 13A as in the first embodiment. However, in this embodiment the collar 18 is removed. In place of the collar 18 is a tight fitting ring seal 18A preferably of an elastomeric material such as silicone rubber which forms a barrier over the top of the boot member 14A and, the compatable, substantially non-porous, cushioning sheath member 16A through which gingival tissue and bony tissue cannot pass and to which gingival tissue will not adhere. This seal 18A may be a thin layer bonded to the root structure 12A and to the upper end of the sheath 16A over the boot member 14A. As in the first embodiment, a resilient porous sleeve or ring member 20A is bonded to the outer surface of tile upper portion 11A adjacent the seal 18A. The resilient member 20A forms an attachment surface for the gingival tissue to provide a barrier against intrusion of bacteria below the seal 18A. In this embodiment the ring seal 18A must be flexible so as to maintain a seal under load conditions while allowing vertical movement of the root structure 12A relative to the cushioning sheath member 16A during mastication. This seal must also not permit bony or gingival tissue to adhere to its surface. If the seal 18A is made of a porous material such as Goretex is used, then the surfaces where there is any area of possible entry must be treated to prevent penetration by living cells and pathogens, e.g. the upper surface of seal 18A and the outer surface of seal 18A. If the seal 18A is silicone rubber and the boot 14A is a porous material (such as Goretex), then the upper end surface of the boot at the interface with seal 18A is treated to prevent penetration by living cells and pathogens.

The dental implant devices 10 and 10A of the invention each provides a cushioned interface between the root structure of the implant and the biocompatible non-porous sheath member 16 or 16A which encloses the resilient boot member 14 or 14A surrounding and in contact with the root structure 12 or 12A. This cushioned interface distributes the force transferred from the tooth to the jaw during mastication by acting as a shock absorber and damping the effect of the stress/shock forces received. Thus, a degree of flexibility and compliance similar to that imparted by the periodontal membrane is given to the dental implant 10 or 10A. It has been determined that without this flexibility a conventional dental implant can cause resorption of the jaw bone and loosening of the implant and trauma to the overlaying tissue which is not desirable because of the possible loss of the implant and the discomfort to the user. Another advantage of this implant flexibility is that manufacturing tolerances required for the prosthesis for proper fit may now be greater due to the flexibility of the implant, thus potentially reducing manufacturing costs.

It will be apparent to those skilled in the art that various modifications and variations can be made in the dental implant of the present invention and in the construction of this implant without departing from the scope or spirit of the invention. Other embodiments of the invention will be apparent to those skilled in the art from the consideration of the specification and practice of the invention disclosed herein. It is intended that the specification and examples be considered as exemplary only, with the true scope and spirit of the invention being indicated by the following claims. All patents and printed publications referred to herein are hereby incorporated by reference in their entirety.

What is claimed is:

1. A dental implant device having a root structure, adapted for use in the oral environment of the mouth having gingival tissue and bony tissue, comprising:

a) said root structure adapted to be implanted in said bony tissue, and having upper and lower portions made of a suitable dental prosthesis material, b) a resilient porous membrane sleeve suitably wrapped about and covering at least the uppermost portion of said root structure, and said resilient porous member sleeve being an attachment surface for gingival tissue;

c) a resilient boot member surrounding and in contact with said lower portion of said root structure, and d) a biocompatible, substantially non-porous, cushioning sheath member enclosing said boot member and said lower portion of said root structure, said sheath member being made of a material to which bony tissue has an affinity; whereby said resilient porous membrane sleeve aiding in providing a seal between said bony tissue and said oral environment of the mouth; and said resilient porous membrane sleeve forming an attachment surface for gingival tissue for providing a barrier against intrusion of bacteria into the bony tissue underlying said dental implant.

2. The dental implant device of claim 1 further comprising a collar connected to and projecting outwardly from said root structure over said boot member and said sheath member.

3. A dental implant device of claim 2, wherein said collar is an integral part of said root structure.

4. The dental implant device of claim 2 wherein said boot member has a flanged upper end that extends outwardly over an upper end of said sheath member between said sheath member and said collar.

5. A dental implant device of claim 4, wherein said collar has a smooth outer surface adapted to act both as a barrier to the growth of bony tissue therealong and as a barrier to the adhesion of gingival tissue.

6. A dental implant device of claim 5, wherein said resilient porous membrane sleeve is attached to the upper portion of said root structure.

7. The dental implant device of claim 1 wherein said porous membrane is made of expanded polytetrafluoroethylene.

8. The dental implant device of claim 1, further comprising a seal between said lower portion of said root structure and an upper end of said sheath member, and over said boot member inside said sheet member.

9. The dental implant device of claim 8, wherein said seal is a ring of elastomeric material around said root structure between said upper and lower portions of said root structure.

10. The dental implant of claim 9, wherein said seal is made of silicone rubber.

11. The dental implant of claim 8, wherein said seal comprises an annular collar between said upper and lower portions of said root structure.

12. The dental implant of claim 11, further comprising a flanged upper end of said root member extending outwardly over the upper end of said sheath member and between said collar and said sheath member so as to form said seal.

13. The dental implant device of claim 12, wherein said boot member is made of silicone rubber.

14. The dental implant device of claim 11, wherein said boot member is made of expanded polytetrafluoroethylene and an outer end surface of said flange is heat sealed.

15. The dental implant device of claim 1, further comprising a seal between said lower portion of said root structure and an upper end of said sheath member, and over said boot member inside said sheath member, and a resilient membrane sleeve around and adhered to said upper portion of said root structure for enhancing adhesion of gingival tissue thereto above said seal.

16. The dental implant device of claim 15, wherein said boot membrane said resilient member and sleeve are made of polytetrafluoroethylene.

17. The dental implant device of claim 15, wherein said seal includes an annular collar between said upper and lower portions of said root structure and a flanged upper end of said boot member extending outwardly over an upper end of said sheath member between said sheet member and said collar.

18. The dental implant device of claim 1, further including a post projecting from said upper portion of said root structure.

19. The dental implant of claim 18, further including a dental prosthesis secured to said post so as to be fixedly disposed in abutting relationship with an upper exposed surface of said root structure and said resilient porous membrane sleeve.

20. The dental implant of claim 1, wherein said resilient porous membrane sleeve is adhesively secured to the upper portion of said root structure.

21. The dental implant of claim 1, wherein said resilient porous membrane sleeve is bondedly secured to the upper portion of said root structure.

* * * * *